US012599335B2

(12) United States Patent
Cho et al.

(10) Patent No.: US 12,599,335 B2
(45) Date of Patent: *Apr. 14, 2026

(54) DETECTION AND MONITORING OF SLEEP APNEA CONDITIONS

(71) Applicant: Medtronic, Inc., Minneapolis, MN (US)

(72) Inventors: Yong K. Cho, Excelsior, MN (US); Eduardo N. Warman, Maple Grove, MN (US); Gautham Rajagopal, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/307,756

(22) Filed: Apr. 26, 2023

(65) Prior Publication Data

US 2023/0363701 A1 Nov. 16, 2023

Related U.S. Application Data

(63) Continuation of application No. 17/116,482, filed on Dec. 9, 2020, now Pat. No. 11,666,271.

(51) Int. Cl.
*A61B 5/00* (2006.01)
*A61B 5/024* (2006.01)
(Continued)

(52) U.S. Cl.
CPC ........ *A61B 5/4818* (2013.01); *A61B 5/02405* (2013.01); *A61B 5/0245* (2013.01);
(Continued)

(58) Field of Classification Search
None
See application file for complete search history.

(56) References Cited

U.S. PATENT DOCUMENTS 6,881,192 B1 4/2005 Park
7,438,686 B2 10/2008 Cho et al.
(Continued)

FOREIGN PATENT DOCUMENTS

CN 204765621 U 11/2015
EP 3071288 B1 11/2018
(Continued)

OTHER PUBLICATIONS

Hayano et al., "Screening for Obstructive Sleep Apnea by Cyclic Variation of Heart Rate," Circulation: Arrhythmia and Electrophysiology, vol. 4, No. 1, Feb. 2011, 9 pp.
(Continued)

*Primary Examiner* — Sana Sahand
(74) *Attorney, Agent, or Firm* — Shumaker & Sieffert, P.A.

(57) ABSTRACT

A method of detecting sleep apnea includes generating a cardiac signal indicating activity of a heart of a patient. The method further includes determining a short-term average heart rate and a long-term average heart rate. The method further includes determining a start and end of a heart rate cycle based on the short-term average heart rate and the long-term average heart rate. The method further includes determining physiological parameter values occurring during the heart rate cycle. The method further includes determining whether patient has or has not experienced a sleep apnea event based on whether one or more conditions are satisfied by one or more parameter values for one or more heart rate cycles and responsively generating an indication that patient has or has not experienced a sleep apnea event.

19 Claims, 5 Drawing Sheets

(51) Int. Cl.

| | |
|---|---|
| *A61B 5/0245* | (2006.01) |
| *A61B 5/349* | (2021.01) |
| *G16H 40/67* | (2018.01) |
| *G16H 50/30* | (2018.01) |
| *A61B 5/29* | (2021.01) |
| *A61B 5/318* | (2021.01) |

(52) U.S. Cl.
CPC ............. *A61B 5/349* (2021.01); *G16H 40/67* (2018.01); *G16H 50/30* (2018.01); *A61B 5/29* (2021.01); *A61B 5/318* (2021.01); *A61B 5/686* (2013.01)

(56) References Cited

U.S. PATENT DOCUMENTS

| | | | |
|---|---|---|---|
| 7,460,899 | B2 | 12/2008 | Almen |
| 8,083,682 | B2 | 12/2011 | Dalal et al. |
| 8,475,388 | B2 | 7/2013 | Ni et al. |
| 8,630,709 | B2 | 1/2014 | Libbus et al. |
| 8,721,560 | B2 | 5/2014 | Koh |
| 8,821,418 | B2 | 9/2014 | Meger et al. |
| 8,998,830 | B2 | 4/2015 | Halperin et al. |
| 9,011,341 | B2 | 4/2015 | Jensen et al. |
| 9,757,560 | B2 | 9/2017 | Papay |
| 10,028,699 | B2 | 7/2018 | Libbus et al. |
| 10,029,098 | B2 | 7/2018 | Papay |
| 10,065,038 | B2 | 9/2018 | Papay |
| 10,265,015 | B2 | 4/2019 | Bardy et al. |
| 10,321,871 | B2 | 6/2019 | Bandyopadhyay et al. |
| 10,595,813 | B2 | 3/2020 | Song et al. |
| 10,744,339 | B2 | 8/2020 | Makansi |
| 2003/0055348 | A1 | 3/2003 | Chazal et al. |
| 2004/0134496 | A1 | 7/2004 | Cho et al. |
| 2005/0119711 | A1* | 6/2005 | Cho ..................... A61B 5/4818 607/42 |
| 2005/0267362 | A1 | 12/2005 | Mietus et al. |
| 2006/0241708 | A1 | 10/2006 | Boute |
| 2007/0032733 | A1 | 2/2007 | Burton |
| 2007/0239055 | A1 | 10/2007 | Sowelam et al. |
| 2010/0262032 | A1 | 10/2010 | Freeberg |
| 2014/0221850 | A1 | 8/2014 | Farringdon et al. |
| 2014/0276928 | A1 | 9/2014 | Vanderpool et al. |
| 2015/0112606 | A1 | 4/2015 | He et al. |
| 2016/0066796 | A1 | 3/2016 | Shinozaki et al. |
| 2016/0310031 | A1 | 10/2016 | Sarkar |
| 2017/0354365 | A1 | 12/2017 | Zhou |
| 2018/0168502 | A1 | 6/2018 | Cho et al. |
| 2019/0059816 | A1 | 2/2019 | Katra et al. |
| 2020/0107775 | A1 | 4/2020 | de Chazal et al. |
| 2020/0147376 | A1 | 5/2020 | Dieken et al. |
| 2020/0269044 | A1 | 8/2020 | Papay |
| 2020/0338358 | A1 | 10/2020 | Makansi |
| 2020/0346017 | A1 | 11/2020 | Caparso et al. |
| 2021/0369191 | A1 | 12/2021 | Gill et al. |
| 2022/0175310 | A1 | 6/2022 | Cho et al. |
| 2025/0064391 | A1 | 2/2025 | Rajagopal et al. |

FOREIGN PATENT DOCUMENTS

| | | |
|---|---|---|
| WO | 2020263451 A1 | 12/2020 |
| WO | 2020263568 A1 | 12/2020 |

OTHER PUBLICATIONS

International Search Report and Written Opinion of International Application No. PCT/US2021/062105, dated Mar. 30, 2022, 15 pp.

Nakayama et al., "Obstructive Sleep Apnea Screening by Heart Rate Variability-Based Apnea/Normal Respiration Discriminant Model," Physiological Measurement, vol. 40, Dec. 20, 2019, 12 pp.

Penzel et al., "Modulations of Heart Rate, ECG, and Cardio-Respiratory Coupling Observed in Polysomnography," Frontiers in Physiology, vol. 7, Article 460, Oct. 25, 2016, 15 pp.

Prosecution History from U.S. Appl. No. 17/116,482, dated Jun. 22, 2022 through Feb. 1, 2023, 64 pp.

Tong et al., "Detection of Sleep Apnea-Hypopnea Syndrome with ECG Derived Respiration in Chinese Population," International Journal of Clinical and Experimental Medicine, vol. 7, No. 5, Jul. 2014, pp. 1269-1275.

* cited by examiner

EXTERNAL
DEVICE
108A

100A

102A

110

106A

104A

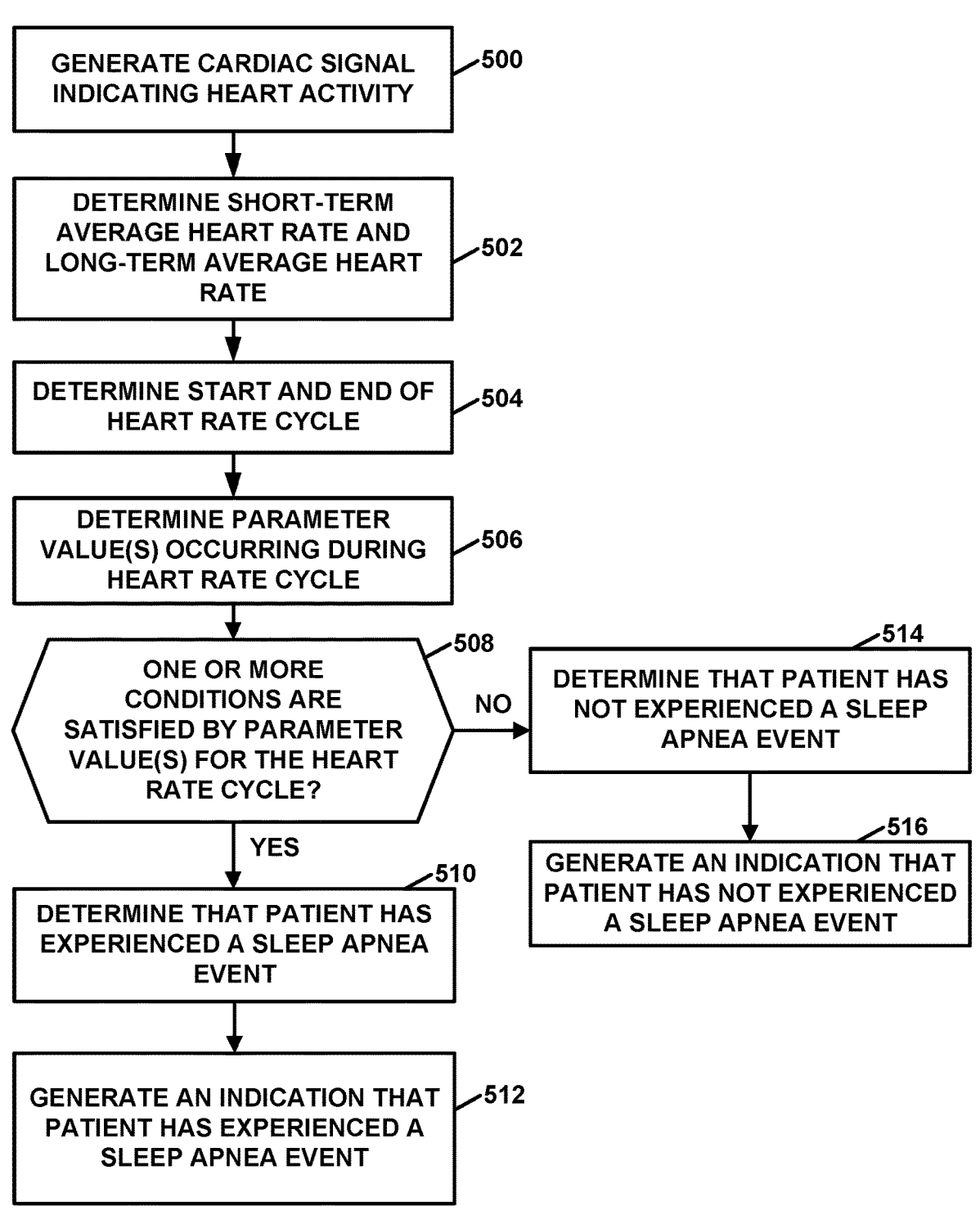

GENERATE CARDIAC SIGNAL INDICATING HEART ACTIVITY ⟋500

DETERMINE SHORT-TERM AVERAGE HEART RATE AND LONG-TERM AVERAGE HEART RATE ⟋502

DETERMINE START AND END OF HEART RATE CYCLE ⟋504

DETERMINE PARAMETER VALUE(S) OCCURRING DURING HEART RATE CYCLE ⟋506

ONE OR MORE CONDITIONS ARE SATISFIED BY PARAMETER VALUE(S) FOR THE HEART RATE CYCLE? ⟋508

NO

DETERMINE THAT PATIENT HAS NOT EXPERIENCED A SLEEP APNEA EVENT ⟋514

GENERATE AN INDICATION THAT PATIENT HAS NOT EXPERIENCED A SLEEP APNEA EVENT ⟋516

YES

DETERMINE THAT PATIENT HAS EXPERIENCED A SLEEP APNEA EVENT ⟋510

GENERATE AN INDICATION THAT PATIENT HAS EXPERIENCED A SLEEP APNEA EVENT ⟋512

FIG. 5

DETECTION AND MONITORING OF SLEEP APNEA CONDITIONS

This application is a continuation of U.S. application Ser. No. 17/116,482, filed Dec. 9, 2020, issued as U.S. Pat. No. 11,666,271, the entire content of which is incorporated herein by reference.

TECHNICAL FIELD

This disclosure generally relates to techniques for monitoring physiological conditions of a patient and, more particularly, to techniques for detecting a sleep apnea episode.

BACKGROUND

When functioning properly, a heart maintains its own intrinsic rhythm, and is capable of pumping adequate blood throughout a circulatory system. This intrinsic rhythm is a function of intrinsic signals generated by the sinoatrial (SA) node located in the upper right atrium. The SA node periodically depolarizes, which in turn causes the atrial heart tissue to depolarize so that right and left atria contract as the depolarization travels through the atrial heart tissue. The atrial depolarization signal is also received by the atrioventricular node, or AV node, which, in turn, triggers a subsequent ventricular depolarization signal that travels through and depolarizes the ventricular heart tissue causing the right and left ventricles to contract.

A condition known as sleep apnea can diminish cardiac output and pose various risks to patients, particularly those who are susceptible to heart failure. Sleep apnea is a sleep disorder that involves the temporary cessation of respiratory airflow during sleep. In various scenarios, sleep apnea may be characterized by one or both of pauses in breathing or periods of shallow breathing during sleep.

Sleep apnea is generally considered a medical syndrome that occurs in various forms. One recognized form of sleep apnea is "central sleep apnea," which is associated with a failure of the central nervous system to automatically initiate and control respiration. Another recognized form of sleep apnea is "obstructive sleep apnea," which is associated with an obstruction of the airways due to airway collapse. Yet another recognized form of sleep apnea is a mixed form that may include a central nervous system failure to drive ventilatory effort combined with an obstructive apnea.

Possible effects of sleep apnea include daytime sleepiness, impaired alertness, and various associated cardiovascular diseases, which in turn can significantly impair patient lifestyle and increase morbidity risk. In some cases, obstructive sleep apnea can lead to death due to lack of oxygen to vital organs of the body. Various approaches have been taken to detect and treat sleep apnea.

SUMMARY

Some existing monitoring systems have relied on respiratory measurement data to detect an episode of sleep apnea. For example, algorithms based on cardiac signals have been used to detect sleep apnea episodes. However, some sleep apnea algorithms have a significant false positive error rate. Thus, there is a need for techniques for accurate detection of sleep apnea episodes.

In one example, the disclosure provides a method of detecting sleep apnea. The method includes sensing, by sensing circuitry, a cardiac signal indicating activity of a heart of a patient. The method further includes determining, by processing circuitry and based on the cardiac signal, a short-term average of a heart rate of the patient and a long-term average of the heart rate of the patient, the short-term average of the heart rate of the patient being based on fewer heart beats than the long-term average of the heart rate of the patient. The method further includes determining, by the processing circuitry, that a heart rate cycle has started based on a first time the short-term average of the heart rate of the patient changes from being less than the long-term average of the heart rate of the patient to being greater than the long-term average of the heart rate of the patient. The method further includes determining, by the processing circuitry, that the heart rate cycle has ended based on a second time the short-term average of the heart rate of the patient changes from being less than the long-term average of the heart rate of the patient to being greater than the long-term average of the heart rate of the patient. The method further includes determining, by the processing circuitry, a peak-to-valley time interval, the peak-to-valley time interval being a time interval between a maximum short-term average of the heart rate during the heart rate cycle and a minimum short-term average of the heart rate during the heart rate cycle. The method further includes determining, by the processing circuitry, whether one or more conditions of a plurality of conditions are satisfied for the heart rate cycle, the plurality of conditions comprising a peak-to-valley time interval condition that the peak-to-valley time interval is greater than a lower peak-to-valley time threshold and less than an upper peak-to-valley time threshold. The method further includes determining, by the processing circuitry, that the patient has experienced a sleep apnea episode based at least in part on one or more conditions being satisfied for the heart rate cycle. The method further includes generating, by the processing circuitry, an indication that the patient has experienced a sleep apnea episode.

In another example, the disclosure provides a system for detecting sleep apnea. The system includes sensing circuitry and processing circuitry. The sensing circuitry is configured to sense a cardiac signal indicating activity of a heart of a patient. The processing circuitry is configured to determine, based on the cardiac signal, a short-term average of a heart rate of the patient and a long-term average of the heart rate of the patient, the short-term average of the heart rate of the patient being based on fewer heart beats than the long-term average of the heart rate of the patient. The processing circuitry is further configured to determine that a heart rate cycle has started based on a first time the short-term average of the heart rate of the patient changes from being less than the long-term average of the heart rate of the patient to being greater than the long-term average of the heart rate of the patient. The processing circuitry is further configured to determine that the heart rate cycle has ended based on a second time the short-term average of the heart rate of the patient changes from being less than the long-term average of the heart rate of the patient to being greater than the long-term average of the heart rate of the patient. The processing circuitry is further configured to determine a peak-to-valley time interval, the peak-to-valley time interval being a time interval between a maximum short-term average of the heart rate during the heart rate cycle and a minimum short-term average of the heart rate during the heart rate cycle. The processing circuitry is further configured to determine whether one or more conditions of a plurality of conditions are satisfied for the heart rate cycle, where one condition of the plurality of conditions is that the peak-to-valley time interval is greater than a lower peak-to-valley time threshold and less than an upper peak-to-valley time threshold. The processing circuitry is further configured to determine that the patient has experienced a sleep apnea episode based at least in part on one or more conditions being satisfied for the heart rate cycle. The processing circuitry is further configured to generate an indication that the patient has experienced a sleep apnea episode.

In another example, the disclosure provides a non-transitory computer-readable storage medium encoded with instructions. The instructions, when executed, cause processing circuitry of a medical device system to receive a cardiac signal indicating activity of a heart of a patient. The instructions further cause the processing circuitry to determine, based on the cardiac signal, a short-term average of a heart rate of the patient and a long-term average of the heart rate of the patient, the short-term average of the heart rate of the patient being based on fewer heart beats than the long-term average of the heart rate of the patient. The instructions further cause the processing circuitry to determine that a heart rate cycle has started based on a first time the short-term average of the heart rate of the patient changes from being less than the long-term average of the heart rate of the patient to being greater than the long-term average of the heart rate of the patient. The instructions further cause the processing circuitry to determine that the heart rate cycle has ended based on a second time the short-term average of the heart rate of the patient changes from being less than the long-term average of the heart rate of the patient to being greater than the long-term average of the heart rate of the patient. The instructions further cause the processing circuitry to determine a peak-to-valley time interval, the peak-to-valley time interval being a time interval between a maximum short-term average of the heart rate during the heart rate cycle and a minimum short-term average of the heart rate during the heart rate cycle. The instructions further cause the processing circuitry to determine whether one or more conditions of a plurality of conditions are satisfied for the heart rate cycle, where one condition of the plurality of conditions is that the peak-to-valley time interval is greater than a lower peak-to-valley time threshold and less than an upper peak-to-valley time threshold. The instructions further cause the processing circuitry to determine that the patient has experienced a sleep apnea episode based at least in part on one or more conditions being satisfied for the heart rate cycle. The instructions further cause the processing circuitry to generate an indication that the patient has experienced a sleep apnea episode.

The details of one or more examples of this disclosure are set forth in the accompanying drawings and in the description below. Other features, objects, and advantages will be apparent from the description and drawings, and from the claims.

4

Figure 3:
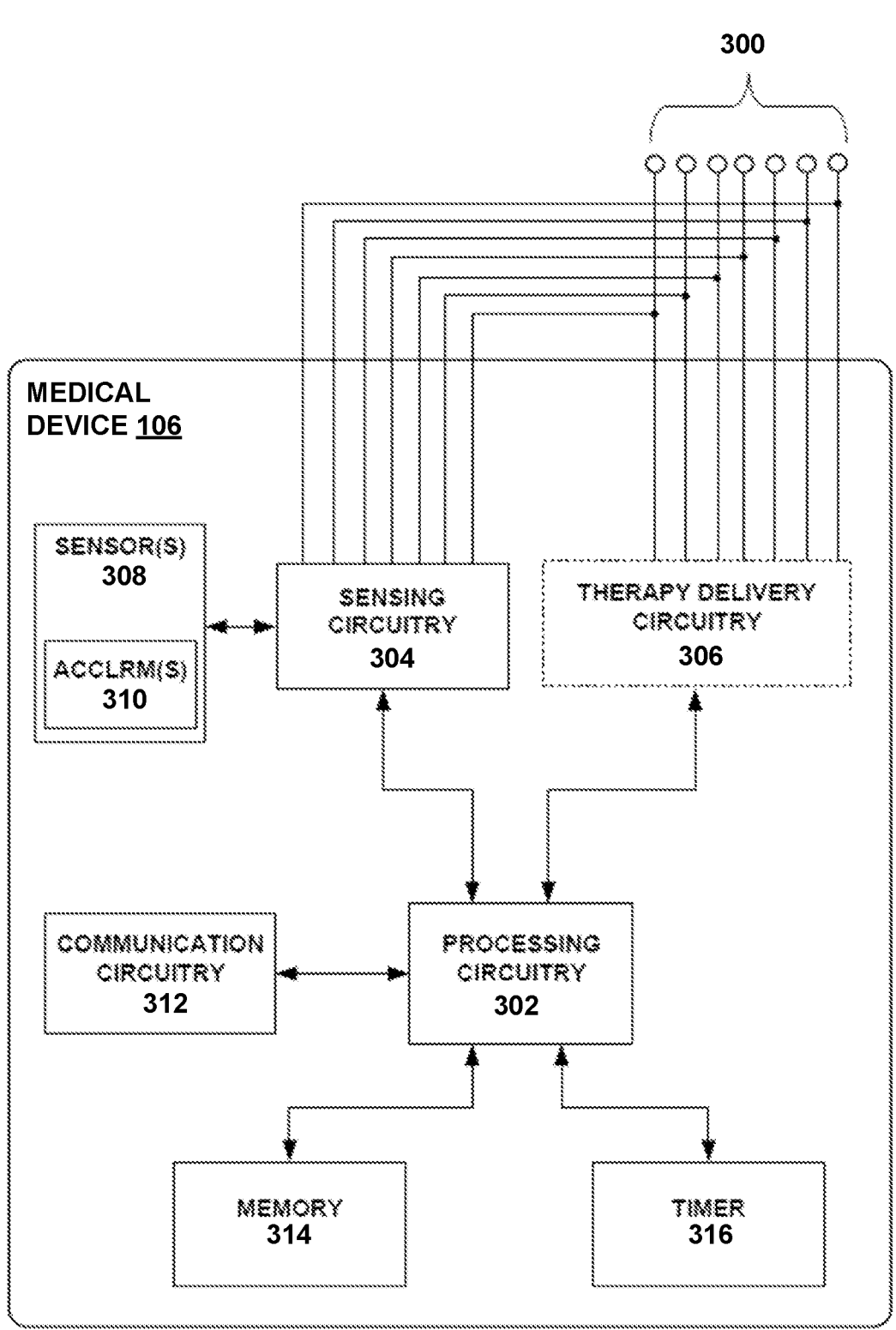

FIG. 3 is a functional block diagram illustrating an example configuration of a medical device configured to sense and record cardiac electrogram signals of a patient.

Figure 4:
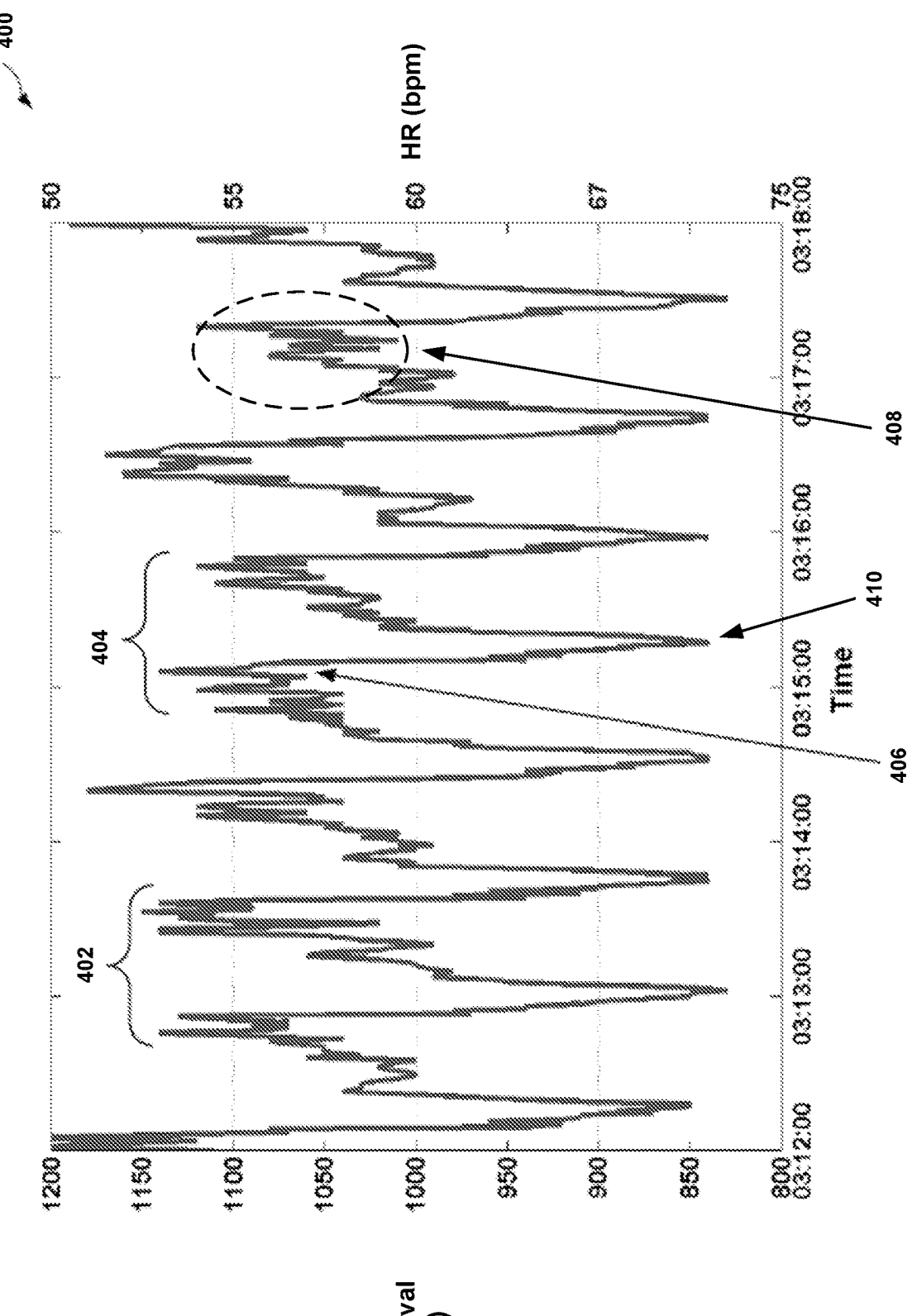

FIG. 4 is a line graph that illustrates sleep disordered heart rate (SDHR) information for a patient.

FIG. 5 is a flowchart illustrating a method by which a medical device system that is configured according to aspects of this disclosure may detect a sleep apnea episode.

DETAILED DESCRIPTION

In general, this disclosure is directed to detecting individual episodes of sleep apnea. Sleep apnea is a breathing disorder that cuts oxygen supply to various systems and organs of the body. To deal with the reduction in oxygenation levels, organs and systems of the body may trigger one or more compensatory mechanisms. With respect to the cardiovascular system, the compensatory mechanism(s) cause the heart to increase blood output for a period of time. As such, the cardiac compensatory mechanisms cause increased exertion of the heart. Moreover, at the end of a sleep apnea episode and during a recovery period that follows a sleep apnea episode, the patient's heart rate may increase significantly, due to alveolar hyperventilation caused by the pulmonary system's compensatory mechanisms. The heart rate spike after a sleep apnea episode may be greater in magnitude naturally occurring heart rate increases that are exhibited by the normal phenomenon of cyclical variation of heart rate (CVHR). As such, both the reduced oxygen supply during a sleep apnea episode and the hyperventilation that follows a sleep apnea episode may cause exertion levels in the heart that exceed normal levels of heart exertion.

The abnormal oxygenation conditions associated with sleep apnea may affect various systems and vital organs adversely. Repeated instances of increased heart exertion, as may be caused by frequent compensatory blood output to counter chronic sleep apnea and by increasing the heart rate to accommodate subsequent hyperventilation, increases the likelihood of heart ailments or possible heart failure. Some existing monitoring systems have relied on respiratory measurement data to detect an episode of sleep apnea. For example, algorithms based on cardiac signals have been used to detect sleep apnea episodes. However, some sleep apnea algorithms may be inaccurate (e.g., have a significant false positive error rate), which may lead to inadequate treatment of sleep apnea.

Techniques described in this disclosure enable a medical monitoring system or therapy delivery system to leverage heart-related data collections to accurately detect, and potentially counter, episodes of sleep apnea. For instance, in one example, sensing circuitry of a medical monitoring system may sense a cardiac signal indicating activity of a heart of a patient. Additionally, processing circuitry of the medical monitoring system may determine, based on the cardiac signal, a short-term average of a heart rate of the patient and a long-term average of the heart rate of the patient, the short-term average of the heart rate of the patient being based on fewer heart beats than the long-term average of the heart rate of the patient.

The processing circuitry may determine that a heart rate cycle has started based on a first time the short-term average of the heart rate of the patient changes from being less than the long-term average of the heart rate of the patient to being greater than the long-term average of the heart rate of the patient. Furthermore, the processing circuitry may determine that the heart rate cycle has ended based on a second time the short-term average of the heart rate of the patient changes from being less than the long-term average of the heart rate of the patient to being greater than the long-term average of the heart rate of the patient.

Additionally, the processing circuitry may determine a series of heart rate variation values (HRV). For example, the processing circuitry may determine, based on heart beats detected during the heart rate cycle, a peak-to-valley heart rate variation value (e.g., the largest difference between a maximum short-term average of the heart rate during the heart rate cycle and a minimum short-term average of the heart rate during the heart rate cycle). That is, the peak-to-valley heart rate variation value may be the largest HRV value of the series of HRV values for the heart rate cycle. The processing circuitry may also determine a peak-to-valley time interval, the peak-to-valley time interval being a time interval between a maximum short-term average of the heart rate during the heart rate cycle and a minimum short-term average of the heart rate during the heart rate cycle.

The processing circuitry may also determine whether one or more conditions of a plurality of conditions are satisfied for one or more heart rate cycles. The plurality of conditions may comprise a peak-to-valley time interval condition that the peak-to-valley time interval is greater than a lower peak-to-valley time threshold and less than an upper peak-to-valley time threshold. The processing circuitry may determine that the patient has experienced a sleep apnea episode based at least in part on one or more conditions being satisfied for one or more heart rate cycles. Furthermore, the processing circuitry may generate an indication that the patient has experienced a sleep apnea episode. Thus, by leveraging heart-related data collections to determine the satisfaction of one or more condition of the plurality of conditions, the medical monitoring system or therapy delivery system may accurately detect, and potentially counter, episodes of sleep apnea.

Figure 1:
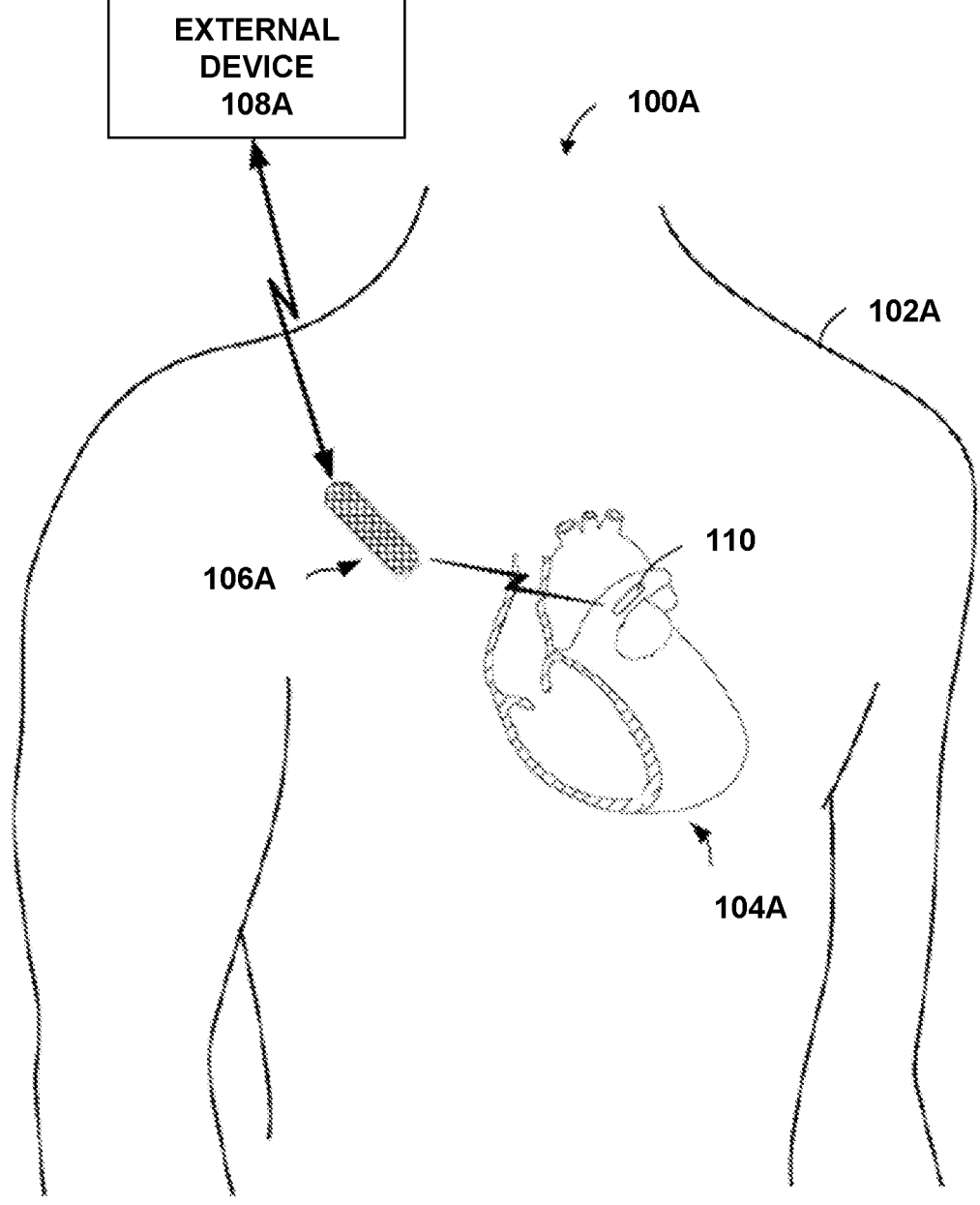
FIG. 1 is a conceptual diagram illustrating an example medical device system in conjunction with a patient, where the medical device system is configured to implement various sleep apnea detection and communication functionalities of this disclosure.
Figure 2:
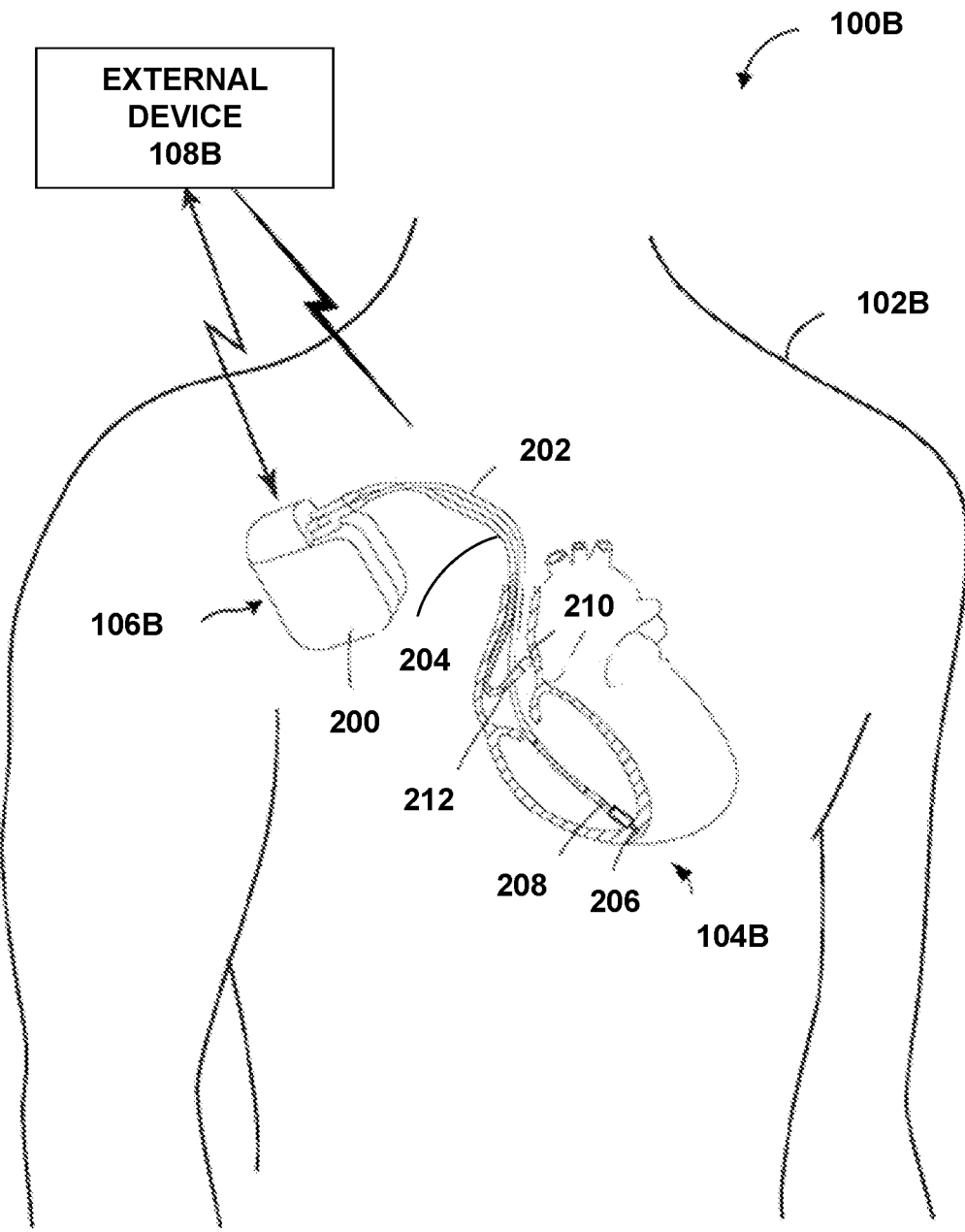
FIG. 2 is a conceptual drawing illustrating another example medical device system in conjunction with a patient, where the medical device system is configured to detect a sleep apnea episode of the patient according to techniques of this disclosure.

FIG. 1 is a conceptual diagram illustrating a medical device system 100A in conjunction with a patient 102A. Medical device system 100A is an example of medical device system 100 configured to implement the techniques described herein for detecting a sleep apnea episode and for responsively providing an indication indicating that the sleep apnea episode is detected. In the example of FIG. 1, medical device system 100A may include a medical device 106A and an external device 108A. Medical device 106A may be an implantable medical device (IMD), such as an insertable cardiac monitor (ICM). In the example of FIG. 2, a medical device system 100B includes a medical device 106B. Medical device 106B may be another implantable medical device, such as an implantable pacemaker. This disclosure may refer to either of medical device 106A or medical device 106B as "medical device 106." In some examples, medical device 106 is an external medical device.

Medical device 106A is capable of sensing and recording cardiac ventricular electrogram (EGM) signals from a position outside of heart 104A. In some examples, medical device 106A may include or be coupled to one or more additional sensors that generate one or more other physiological signals, such as signals that vary based on heart motion and/or sounds, blood pressure, blood flow, blood oxygenation, or respiration. Medical device 106A may be implanted outside of the thorax of patient, e.g., subcutaneously or submuscularly, such as the pectoral location illustrated in FIG. 2. In some examples, medical device 106A may take the form of a Reveal LINQ™ ICM.

External device 108A may be a computing device, e.g., used in a home, ambulatory, clinic, or hospital setting, to communicate with medical device 106A via wireless telemetry. External device 108A may be coupled to a remote patient monitoring system, such as Carelink®. External device 108A may be, for example, a programmer, external monitor, or consumer device (e.g., smart phone), etc. External device 108A may be used to program commands or operating parameters into medical device 106A for controlling its functioning, e.g., when configured as a programmer for medical device 106A. External device 108A may be used to interrogate medical device 106A to retrieve data, including device operational data as well as physiological data accumulated in memory. The interrogation may be automatic, e.g., according to a schedule, or in response to a remote or local user command. Programmers, external monitors, and consumer devices are examples of external devices 30A that may be used to interrogate medical device 106A. Examples of communication techniques used by medical device 106A and external device 108A may include tissue conductance communication (TCC), or radiofrequency (RF) telemetry, which may be an RF link established via Bluetooth®, WiFi®, or medical implant communication service (MICS). Medical device system 100A also may include implantable sensing device 110, also referred to as sensor device 110.

External device 108A may wirelessly communicate with medical device 106A, e.g., to program the functionality of the ICM, and to retrieve recorded physiological signals and/or patient parameter values or other data derived from such signals from the ICM. Both medical device 106A and external device 108A may include processing circuitry, and the processing circuitry of either device, of both devices, or any other device included in medical device system 100A may perform the techniques described herein, such as determining patient parameter values for a period and determining whether one or more patient parameter values is indicative of a sleep apnea episode.

Based on the analysis of patient's heart activity, the processing circuitry of one or more of the devices may also be configured to provide an indication to a user, e.g., to a clinician and/or to patient 102A that a likely sleep apnea episode has been detected, e.g., via external device 108A. For example, medical device system 100A may store (e.g., record) data associated with the occurrence of the likely sleep apnea episode in memory (e.g., as illustrated in FIG. 3) included in medical device system 100A (e.g., memory of either medical device 106A or external device 108A, or any other memory included in medical device system 100A, such as memory included in a server, etc.). Medical device system 100A may then automatically present (e.g., at a pre-determined time of day) the data (e.g., as part of a report or history of patient 102A) in response to input from patient 102A or another person. For example, patient 102A or another person may press a button to cause medical device system 102A to present the data in a visual form (e.g., display the data via a display, etc.), audio form (e.g., emit a sound, etc.), tactile form (e.g., vibration or vibrational pattern, etc.), and/or any other form suitable for communicating information to patient 102A. Patient 102A, a clinician, or another implanted or external medical device may use the data to deliver or take a preventative measure to prevent the occurrence of additional sleep apnea episodes.

Medical device 106A may monitor physiological parameter value(s) indicative of patient state, such as heart rate, HRV values, peak-to-valley time intervals, activity count, peak-to-valley heart rate variation values, cycle lengths, etc.

Medical device 106A may measure the physiological parameter value(s) all the time or at specific times of the day and/or night. In some examples, sensor device 110 may be a part of sensor assembly 106A. Each of sensor device 110 and medical device 106A may include a timer and processing circuitry configured to determine a time of day based on the timer value. If sensor device 110 determines that the current time is within a predetermined window that may be stored in memory of sensor device 110, sensor device 110 may measure and transmit the physiological parameter value(s) of patient to medical device 106A.

In some examples, sensor device 110 may include wireless communication circuitry configured to receive a trigger signal from medical device 106A. The pressure sensing circuitry of sensor device 110 may be configured to measure the physiological parameter value(s) of patient in response to receiving the trigger signal. In this manner, medical device 106A may dictate the times at which sensor device 110 measures physiological parameter value(s), and sensor device 110 may enter a low-power mode such as sleep mode until the wireless communication circuitry of sensor device 110 receives a trigger signal. Medical device 106A may transmit physiological parameter data (e.g., heart rate, HRV values, peak-to-valley time intervals, activity count, peak-to-valley heart rate variation values, cycle lengths, etc.) acquired by medical device 106A to external device 108A. Medical device 106A may also transmit physiological parameter value(s) measurements received from sensor device 110 to external device 108A.

Although not illustrated in the example of FIG. 1, a medical device system configured to implement the techniques described in this disclosure may include one or more implanted or external medical devices in addition to or instead of medical device 106A. For example, a medical device system may include a vascular ICD, an extravascular ICD, a cardiac pacemaker implanted outside of the heart 104A but coupled to intracardiac or epicardial leads, or an intracardiac pacing device. One or more such devices may generate signals, and include processing circuitry configured to perform, in whole or in part, the techniques described herein for detecting sleep apnea episode(s). The implanted devices may communicate with each other and/or an external device 108A, and one of the implanted or external devices may ultimately determine whether sleep apnea is detected based on information received from the other device(s).

In various examples, implantable medical device (IMD) components may be connected to leads that extend into heart 104A or could be implanted in heart 104A entirely. In some examples, components of medical device system 100A may be external devices. Components of medical device system 100A may be configured to detect cardiac electrogram signals, such as an ECG. In various examples, processing circuitry of medical device system 100A, such as processing circuitry of medical device 106A and/or external device 108A, may perform the techniques of this disclosure using various types of sensing circuitry, such as sensing circuitry of medical device 106A and/or sensing circuitry of sensor device 110 capable of detecting timing of cardiac depolarization or contraction. As such, aspects of medical device system 200A may detect sleep apnea episodes using various types of measurements, such as cardiac cycle metrics sensed by medical device 106A and/or pressure-based readings sensed by sensor device 110.

FIG. 2 is a conceptual drawing illustrating an example medical device system 100B in conjunction with a patient 102B. Medical device system 100A and medical device system 100B (either of which may be referred to as "medical device system 100") are examples of medical device systems configured to implement the techniques described herein for detecting a sleep apnea episode based on whether one or more physiological parameter values (e.g., peak-to-valley time interval, activity count, peak-to-valley heart rate variation value, cycle length, etc.) satisfy one or more conditions (e.g., the peak-to-valley time interval condition, the activity count condition, the peak-to-valley heart rate variation condition, the cycle length condition, etc.). In some examples, upon identifying a likely sleep apnea episode, components of medical device system 100B may also responsively provide an indication indicating that a sleep apnea episode is likely occurring, and/or deliver a therapy configured to prevent, mitigate, or remedy the effects of the sleep apnea episode. In the illustrated example, medical device system 100B includes medical device 106B coupled to a ventricular lead 202 and an atrial lead 204.

Ventricular lead 202 and atrial lead 204 may be electrically coupled to medical device 106B and extend into the patient's heart 104B. Ventricular lead 202 may include electrodes 206 and 208 shown positioned on the lead in the patient's right ventricle (RV) for sensing EGM signals and pacing in the RV. Atrial lead 204 may include electrodes 210 and 212 positioned on the lead in the patient's right atrium (RA) for sensing atrial EGM signals and pacing in the RA.

Medical device 106B may use both ventricular lead 202 and atrial lead 204 to acquire cardiac electrogram (EGM) signals from heart 104B of patient 102B. Medical device system 100B is shown as having a dual chamber IMD configuration, but other examples may include one or more additional leads, such as a coronary sinus lead extending into the right atrium, through the coronary sinus and into a cardiac vein to position electrodes along the left ventricle (LV) for sensing LV EGM signals and delivering pacing pulses to the LV. In other examples, a medical device system may be a single chamber system, or otherwise not include atrial lead 204.

Processing circuitry, sensing circuitry, and other circuitry configured for performing the techniques described herein may be housed within a sealed housing 200 of medical device 106B. Housing 200 (or a portion thereof) may be conductive to serve as an electrode for pacing or sensing. Medical device 106B may acquire signal data (e.g., EGM signal data) and cardiac rhythm episode data and transmit the data to an external device 108B. External device 108B may be a computing device, e.g., a device used in a home, ambulatory, clinic, or hospital setting, comprising processing circuitry and/or communicative interfacing circuitry configured to communicate with medical device 106B via wireless telemetry. External device 108B may be coupled to a remote patient monitoring system, such as Carelink®. External device 108B may include, be, or may be part of, in various examples, a programmer, external monitor, or consumer device, e.g., a smart phone.

External device 108B may be implemented and may operate in a manner similar to external device 108A. For example, external device 108B may be used to program commands or operating parameters into medical device 106B for controlling its functioning, e.g., when configured as a programmer for medical device 106B, and may be used to interrogate medical device 106B to retrieve data, including device operational data as well as physiological data accumulated in a memory of medical device 106B. Medical device system 100B is an example of a medical device system operable to leverage physiological parameter value(s) to detect sleep apnea episodes. For example, medical device system 100B may be configured to monitor physiological parameter value(s) and determine whether one or more physiological parameter value satisfy one or more conditions. In some examples, if medical device system 100B determines that a sleep apnea episode has likely occurred, medical device system 100B may responsively provide an indication indicating that the event is detected, and optionally, trigger delivery of a therapy configured to remediate the effects of the event or stem the progression of such effects. The techniques may be performed by processing circuitry of medical device system 100B, such as processing circuitry of one or both of medical device 106B and external device 108B, individually, or collectively.

The processing circuitry of external device 108B and/or medical device 106B may determine the values of at least some patient parameters based on signals generated by sensing circuitry of medical device 106B. In some examples, medical device 106B may include or be coupled to one or more other sensors that generate one or more other physiological signals, such as signals that vary based on blood flow and/or respiration. The processing circuitry of external device 108B and/or medical device 106B may determine patient parameters based on therapy delivered by various components of medical device system 2B that are omitted from FIG. 2 for ease of illustration, such as a CPAP machine. For instance, the processing circuitry of external device 108B and/or medical device 106B may analyze heart activity information to determine whether a sleep apnea episode has been remediated effectively by way of therapy delivered by the positive airway pressure machine or medical device 106B.

FIG. 3 is a functional block diagram illustrating an example configuration of a medical device 106. Medical device 106 may correspond to medical device 106A in FIG. 1, medical device 106B illustrated in FIG. 2, or another medical device configured to implement the techniques as described in this disclosure. Similarly, although not illustrated in FIG. 3, external device 108 may correspond to external device 108A in FIG. 1, external device 108B illustrated in FIG. 2, or another external device configured to implement the techniques as described in this disclosure.

In the illustrated example, medical device 106 includes processing circuitry 302, memory 314, sensing circuitry 304, therapy delivery circuitry 306, one or more sensors 308 (e.g., an accelerometer 310), communication circuitry 312, and timer 316. However, medical device 106 does not need to include all these components in some examples, or medical device 106 may include additional components in some examples. For example, medical device 106 may not include therapy delivery circuitry 306 in some instances.

Memory 314 may include computer-readable instructions that, when executed by processing circuitry, cause medical device 106 and processing circuitry to perform various functions attributed to medical device 106 and processing circuitry herein (e.g., determining time of day, comparing time of day to a predetermined window, causing communication circuitry 312 to transmit physiological parameter value(s) to an external device, etc.). Memory 314 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media. Memory 314 may store threshold(s) for the peak-to-valley time interval condition, the activity count condition, the peak-to-valley heart rate variation condition, the cycle length condition, etc.

Memory 314 may also store data indicating physiological parameter value(s) measurements received from sensing device 110.

Processing circuitry 302 may include fixed function circuitry and/or programmable processing circuitry. Processing circuitry 302 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 302 may include multiple components, such as any combination of one or more microprocessors, one or more controllers, one or more DSPs, one or more ASICs, or one or more FPGAs, as well as other discrete or integrated logic circuitry. The functions attributed to processing circuitry 302 herein may be embodied as software, firmware, hardware or any combination thereof. For example, processing circuitry 302 may be processing circuitry of either medical device 106 or external device 108 or any other processing circuitry included in medical device system 100 may be configured to perform techniques in accordance with this disclosure, such as determining patient parameter values for a period and determining whether one or more patient parameter values are indicative of a sleep apnea episode.

Sensing circuitry 304 and therapy delivery circuitry 306 are coupled to electrodes 300. Electrodes 300 illustrated in FIG. 3 may correspond to, for example, electrodes carried on leads 202 and/or 204 of medical device system 200B (FIG. 2). Sensing circuitry 304 may monitor signals from a selected two or more of electrodes 300 in order to monitor electrical activity of heart, impedance, or other electrical phenomenon. Sensing of a cardiac electrical signal may be done to determine heart rates or HRV, or to detect arrhythmias (e.g., tachyarrhythmias or bradycardia) or other electrical signals. In some examples, sensing circuitry 304 may include one or more filters and amplifiers for filtering and amplifying a signal received from electrodes 300. In some examples, sensing circuitry 304 may sense or detect physiological parameters, such as heart rate, blood pressure, respiration, and the like.

The resulting cardiac electrical signal may be passed to cardiac event detection circuitry that detects a cardiac event when the cardiac electrical signal crosses a sensing threshold. The cardiac event detection circuitry may include a rectifier, filter and/or amplifier, a sense amplifier, comparator, and/or analog-to-digital converter.

Sensing circuitry 304 may also include a switch module to select which of the available electrodes 300 (or electrode polarities) are used to sense the heart activity. In examples with several electrodes 300, processing circuitry 302 may select the electrodes that function as sense electrodes, i.e., select the sensing configuration, via the switch module within sensing circuitry 304. Sensing circuitry 304 may also pass one or more digitized EGM signals to processing circuitry 302 for analysis, e.g., for use in cardiac activity discrimination (e.g., cardiac rhythm discrimination).

In the example of FIG. 3, medical device 106 includes one or more sensors 308 coupled to sensing circuitry 304. Although illustrated in FIG. 3 as being included within medical device 106, one or more of sensors 308 may be external to medical device 106, e.g., coupled to medical device 106 via one or more leads, or configured to wirelessly communicate with medical device 106. In some examples, sensors 308 transduce a signal indicative of a patient parameter, which may be amplified, filtered, or otherwise processed by sensing circuitry 304. In such examples, processing circuitry 302 determines physiological parameter value(s) based on the signals. In some examples, sensors 308 determine the physiological parameter value(s), and communicate them, e.g., via a wired or wireless connection, to processing circuitry.

In some examples, sensors 308 include one or more accelerometers 310, e.g., one or more three-axis accelerometers. Signals generated by the one or more accelerometers 310 may be indicative of, for example, heart sounds or other vibrations or movement associated with the beating of the heart, or coughing, rales, or other respiration abnormalities. Accelerometers 310 may produce and transmit signals to processing circuitry 302 for a determination as to whether the heart 104 has contracted. In some examples, sensors 308 may include one or more microphones configured to detect heart sounds or respiration abnormalities. In some examples, sensors 308 may include sensors configured to transduce signals indicative of blood flow, oxygen saturation of blood, or patient temperature, and processing circuitry may determine patient parameters values based on these signals.

Therapy delivery circuitry 306 is configured to generate and deliver electrical therapy to the heart. Therapy delivery circuitry 306 may include one or more pulse generators, capacitors, and/or other components capable of generating and/or storing energy to deliver as pacing therapy, defibrillation therapy, cardioversion therapy, other therapy or a combination of therapies. In some instances, therapy delivery circuitry 306 may include a first set of components configured to provide pacing therapy and a second set of components configured to provide anti-tachyarrhythmia shock therapy. In other instances, therapy delivery circuitry 306 may utilize the same set of components to provide both pacing and anti-tachyarrhythmia shock therapy. In still other instances, therapy delivery circuitry 306 may share some of the pacing and shock therapy components while using other components solely for pacing or shock delivery.

Therapy delivery circuitry 306 may include charging circuitry, one or more charge storage devices, such as one or more capacitors, and switching circuitry that controls when the capacitor(s) are discharged to electrodes 300 and the widths of pulses. Charging of capacitors to a programmed pulse amplitude and discharging of the capacitors for a programmed pulse width may be performed by therapy delivery circuitry 306 according to control signals received from processing circuitry, which are provided by processing circuitry according to parameters stored in memory 314. Processing circuitry may control therapy delivery circuitry 306 to deliver the generated therapy to the heart via one or more combinations of electrodes 300, e.g., according to parameters stored in memory 314. Therapy delivery circuitry 306 may include switch circuitry to select which of the available electrodes 300 are used to deliver the therapy, e.g., as controlled by processing circuitry.

Communication circuitry 312 may include any suitable hardware, firmware, software or any combination thereof for communicating with another device, such as an external device 108 or another IMD or sensor. Under the control of processing circuitry, communication circuitry 312 may receive downlink telemetry from and send uplink telemetry to an external device 108 or another device with the aid of an antenna, which may be internal and/or external. In some examples, communication circuitry 312 may communicate with a local external device, and processing circuitry may communicate with a networked computing device via the local external device and a computer network, such as the Medtronic CareLink® Network.

A clinician or other user may retrieve data from medical device 106 using external device 108A or another local or networked computing device configured to communicate with processing circuitry via communication circuitry 312. The clinician may also program parameters of medical device 106 using external device 108 or another local or networked computing device.

Communication circuitry 312 may also be configured to communicate with an implantable pressure sensing device 110. Processing circuitry may receive measured physiological parameter value(s) values from sensing device 110 via communication circuitry 312. In some examples, processing circuitry may send a trigger signal to sensing device 110 via communication circuitry 312 to control the sensing device to measure physiological parameter value(s) in response to the trigger signal.

Although not illustrated in FIG. 3, communication circuitry 312 may be coupled to electrodes 300 for tissue conductance communication (TCC) via the electrodes. In some examples, communication with medical device 106 and external device 108 may be via RF telemetry or TCC. In one example, communication circuitry 312 may be configured for RF telemetry communication with external device 108 and TCC with sensing device 110.

Medical device 106 and/or external device 108 may include timer 316. Timer 316 may be configured to provide a timer value, which processing circuitry may use to measure and determine various physiological parameters that involve duration (e.g., HRV, cycle length, etc.). Additionally or alternatively, processing circuitry 302 may determine a time of day based on the timer value. For example, processing circuitry 302 may be configured to determine a time of day based on the timer value. Processing circuitry 302 may associate heart activity of the patient with the time of day when the heart activity occurred. For example, processing circuitry may associate one or more sleep apnea episodes with the time of day when the sleep apnea episodes occurred and store this information in memory 314, which may be retrieved, for example, during interrogation by external device 108.

FIG. 4 is a line graph 400 that illustrates sleep disordered heart rate (SDHR) information for patient. In FIG. 4, the R-R interval corresponds to the interval between two successive R-waves. In the example of line graph 400, the SDHR of patient exhibits, at various times, characteristics of different physiological conditions. For instance, the processing circuitry of medical device system 100A or 100B (collectively "medical device system 100"), such as processing circuitry of a medical device 106 and/or external device 108, may analyze trends shown by clusters of maxima and minima (e.g., "peak" and "valley") points of line graph 400 to determine whether patient exhibits symptoms of a sleep apnea episode. Some peak-and-valley clusters that the processing circuitry of medical device system 100 may analyze to detect possible sleep apnea episodes with respect to a patient are identified in FIG. 4.

For example, even during normal breathing, the heart rate information of line graph 400 illustrates a type of cyclical variable heart rate (CVHR) referred to as respiratory sinus arrhythmia (RSA). During RSA, the heart rate of the patient increases with an inspiration (or inhalation) and the heart rate of patient decreases with expiration (or exhalation). RSA is associated with a single breath cycle, e.g., a single heart rate increase with inspiration and a single heart rate decrease with expiration. RSA is illustrated in the graph of FIG. 4 by higher frequency and lower amplitude variations 408.

The lower frequency and higher amplitude variations of the graph of FIG. 4, on the other hand, illustrate a form of CVHR, referred to herein as SDHR, associated with sleep apnea. For example, each of areas 402 and 404 illustrates one apnea arousal cycle, and the corresponding decrease and increase in heart rate. In most patients, a decrease of heart rate is observed during each apnea event followed by an increase of heart rate near the end of the apnea event. The heart rate further increases during ensuing hyperventilation. In the example of the individual sleep apnea episode associated with area 404 of line graph 400, the heart rate increase due to autonomic arousal is indicated by crest 406. For instance, crest 406 may indicate a decrease that heart 104 experiences as the autonomic nervous system of patient attempts to compensate for the increased oxygen saturation during recovery from a sleep apnea episode. As such, troughs between such crests may be indicative of a period of overexertion of heart 104 which results from compensatory mechanisms that the autonomic nervous system of patient implements to counter the decreased oxygen saturation caused by the sleep apnea episode. As shown in FIG. 4, near the end of the sleep apnea episode (e.g., after a valley 410), the heart rate may increase.

Again, the processing circuitry of medical device system 100 may collect and analyze physiological parameter value(s), determined in any way, to identify sleep apnea events based on the characteristics illustrated by the line graph 400 of FIG. 4.

FIG. 5 is a flowchart illustrating a method by which a medical device system 100 that is configured to perform techniques described in this disclosure may detect a sleep apnea episode. In accordance with techniques of this disclosure, medical device system 100 may generate, by processing circuitry 302, a cardiac signal indicating activity of a heart of patient 102 in response to signals sensed by sensing circuitry 304 of medical device 106. As discussed above, processing circuitry 302 may be included in medical device 106, external device 108, or elsewhere in medical device system 100. Medical device 106 may include one or more sensors 308 configured to sense signals produced by heart activity. Sensing circuitry 304 may deliver (e.g., send, transmit, etc.) detected signals to processing circuitry 302. Processing circuitry 302 may then generate (e.g., based on an algorithm) a cardiac signal indicating the activity of a heart of patient 102. In some examples, the cardiac signal may be associated with characteristics of the heart activity of patient 102. For example, the cardiac signal may be associated with the waves, intervals, durations, and rhythm of the heart activity of patient 102.

Medical device system 100 may further determine, by processing circuitry 302, a short-term average heart rate and a long-term average heart rate upon which the start and end of a heart rate cycle may be based (502). The short-term average of the heart rate of patient 102 may be based on a first number of heartbeats, and the long-term average of the heart rate of patient 102 may be based on a second number of heartbeats, wherein the first number is less than the second number. For example, the first number of heartbeats may be equal to 3 heartbeats and the second number of heartbeats may be equal to 120 heartbeats. In such an example, the short-term average of the heart rate of patient 102 may be based on 3 heartbeats, and the long-term average of the heart rate of patient 102 may be based on 120 heartbeats. In other examples, the first number of heartbeats may be equal to a value other than 3 (e.g., 4, 5, etc.) and/or the second number of heartbeats may be equal to a value other than 120 (e.g., 119, 130, etc.).

Medical device system 100 may further calculate, by processing circuitry 302, the short-term average of the heart rate and the long-term average of the heart rate may vary. For example, the short-term average of the heart rate and the long-term average of the heart rate may be the median of the first number of heartbeats and the second number of heartbeats, respectively (e.g., the median of 3 heartbeats and the median of 120 heartbeats, respectively). Alternatively, the short-term average of the heart rate and the long-term average of the heart rate may be the mean of the first number of heartbeats and the second number of heartbeats, respectively (e.g., the mean of 3 heartbeats and the mean of 120 heartbeats, respectively). Alternatively, the short-term average of the heart rate and the long-term average of the heart rate may be the mode of the first number of heartbeats and the second number of heartbeats (e.g., the mode of 3 heartbeats and the mode of 120 heartbeats, respectively). It should be understood that other methods for calculating the short-term average of the heart rate and the long-term average of the heart rate may be appropriate depending upon the circumstances.

Processing circuitry 302 of medical device system 100 may further determine the start and end of a heart rate cycle (504). The heart rate cycle defines a period of time of the patient 102's heart activity that is being processed by processing circuitry 302 to detect the occurrence of a sleep apnea episode. The start of the heart rate cycle may be based on a first time the short-term average of the heart rate of patient 102 changes from being less than the long-term average of the heart rate of patient 102 to being greater than the long-term average of the heart rate of patient 102. For example, if the long-term average of the heart rate of patient 102 is a constant 65 beats per minute (BPM), then the start of the heart rate cycle may be determined based on the first time that the short-term average of the heart rate of patient 102 exceeds 65 BPM. Similarly, the end of the heart rate cycle may be based on the second time the short-term average of the heart rate of patient 102 changes from being less than long-term average of the heart rate of patient 102 to being greater than the long-term average of the heart rate of patient 102. For example, if the long-term average of the heart rate of patient 102 is a constant 65 BPM, then the end of the heart rate cycle may be determined based on the second time that the short-term average of the heart rate of patient 102 exceeds 65 BPM.

Processing circuitry 302 of medical device system 100 may further determine parameter values for patient 102 based on heart activity occurring during the heart rate cycle (506). Determining whether patient 102 has experienced a sleep apnea episode may be based on one or more parameter values.

The parameter values to be determined by processing circuitry 302 may include a peak-to-valley time interval. The peak-to-valley time interval is the time interval between a maximum short-term average of the heart rate during the heart rate cycle and a minimum short-term average of the heart rate during the heart rate cycle. For example, if a maximum short-term average of the heart rate value of 75 BPM occurs 30 seconds from a reference point (e.g., the beginning of a recording of the heart rate cycle, the beginning of the heart rate cycle, etc.) and during the heart rate cycle and the minimum short-term heart rate average value of 60 BPM occurs 45 seconds from the reference point and during the heart rate cycle, then the peak-to-valley time interval is equal to 15 seconds.

The parameter values to be determined by processing circuitry 302 may further include an activity count. The activity count for the heart rate cycle indicates a number of time intervals during the heart rate cycle in which an amount of movement of the patient 102 is greater than a minimum movement threshold. Amount of movement of patient 102 may be determined using one or more sensors 308 (e.g., accelerometer 310). For example, accelerometer 310 may measure the acceleration of patient's body, and if the acceleration of patient's body exceeds an acceleration threshold corresponding to a minimum movement threshold, the activity count for the heart rate cycle may be incremented by one. As such, if, in a single heart rate cycle, the acceleration of patient's body exceeds the acceleration threshold 8 times, the minimum movement threshold may also be exceeded 8 times so that the activity count for patient 102 is 8.

The parameter values to be determined by processing circuitry may further include a peak-to-valley heart rate variation value. The peak-to-valley heart rate variation value for the heart rate cycle is the difference between a maximum short-term average of the heart rate during the heart rate cycle and a minimum short-term average of the heart rate during the heart rate cycle. For example, if the maximum short-term average of the heart rate during the heart rate cycle is 75 BPM and the minimum short-term average of the heart rate during the heart rate cycle is 60 BPM, then the peak-to-valley heart rate variation value is 15 BPM for this heart rate cycle.

The parameter values to be determined by processing circuitry 302 may further include a cycle length, where the cycle length for the heart rate cycle indicates a length of the heart rate cycle. For example, if the start of the heart rate cycle is at first time of 0 seconds (e.g., based on the first time that the short-term average of the heart rate of patient 102 exceeds the long-term average of the heart rate of patient 102), and the end of the heart rate cycle is at second time of 70 seconds (e.g., based on the second time that the short-term average of the heart rate of patient 102 exceeds the long-term average of the heart rate of patient 102), the cycle length is 70 seconds.

In some examples, processing circuitry 302 may use a parameter value to determine another parameter value. For example, processing circuitry 302 may use a series of heart rate values to determine the peak-to-valley time interval, which in turn may be used to determine whether patient 102 experienced a sleep apnea episode. For example, if the short-term average of the heart rate of patient 102 fluctuates from 70 BPM to 60 BPM, 60 BPM to 85 BPM, 85 BPM to 65 BPM, and so on during the heart cycle, heart rate values may include 10 BPM (70 BPM less 60 BPM), 25 BPM (85 BPM less 60 BPM), 5 BPM (70 BPM less 65 BPM), and so on. In this example, the peak-to-valley variation value is 25 BPM because 85 BPM is the maximum short-term heart rate average value during the heart rate cycle, and 60 BPM is the minimum short-term average value during the heart rate cycle.

Processing circuitry 302 may then use the respective times the maximum short-term average of the heart rate value of 85 BPM and the minimum short-term average of the heart rate value of 60 BPM occurred to determine the peak-to-valley time interval. For example, if the maximum short-term average of the heart rate value of 85 BPM occurred 30 seconds from the start of the heart rate cycle and the minimum short-term average of the heart rate value of 60 BPM occurred 60 seconds from the start of the heart rate cycle, then the peak-to-valley time interval is equal to 30 seconds.

Processing circuitry 302 of medical device system 100 may further determine whether one or more conditions of a plurality of conditions are satisfied by one or more parameter values for patient 102 for the heart rate cycle. The plurality of conditions may include, but is not limited to, a peak-to-valley time interval condition, an activity count condition, a peak-to-valley heart rate variation condition, a cycle length condition, etc.

The plurality of conditions may include a peak-to-valley time interval condition. The peak-to-valley time interval condition may be a condition that the peak-to-valley time interval is greater than a lower peak-to-valley time threshold and less than an upper peak-to-valley time threshold. For example, if the lower peak-to-valley time threshold is equal to 5 seconds and the upper peak-to-valley time threshold is equal to 30 seconds, then processing circuitry 302 may determine that the peak-to-valley time interval condition is satisfied if the peak-to-valley time interval is greater than 5 seconds and less than 30 seconds. As such, a peak-to-valley time interval of 10 seconds, for example, would satisfy the peak-to-valley time interval condition. Alternatively, processing circuitry 302 may determine that the peak-to-valley time interval condition is not satisfied if the peak-to-valley time interval is not greater than 5 seconds and less than 30 seconds. As such, a peak-to-valley time interval of 3 seconds, for example, would not satisfy the peak-to-valley time interval condition.

Additionally or alternatively, the plurality of conditions may include an activity count condition. The activity count condition may be a condition that an activity count for the heart rate cycle is less than an activity count threshold. For example, if the activity count threshold is equal to 8, then processing circuitry 302 may determine that the activity count condition is satisfied if the activity count is less than 8. As such, an activity count of 5, for example, would satisfy the activity count condition. Alternatively, processing circuitry 302 may determine that the activity count condition is not satisfied if the activity count is not less than 8. As such, an activity count of 10, for example, would not satisfy the activity count condition.

Additionally or alternatively, the plurality of conditions may include a peak-to-valley HRV condition. The peak-to-valley HRV condition may be a condition that the peak-to-valley HRV value for the heart rate cycle is greater than a lower peak-to-valley heart rate variation threshold and less than an upper peak-to-valley heart rate variation threshold. For example, if the lower peak-to-valley heart rate variation threshold is equal to 6 BPM and the upper peak-to-valley heart rate variation threshold is equal to 50 BPM, then processing circuitry 302 may determine that the peak-to-valley HRV condition is satisfied if the peak-to-valley HRV value is greater than 6 and less than 50. As such, a peak-to-valley HRV value of 25, for example, would satisfy the peak-to-valley HRV condition. Alternatively, processing circuitry 302 may determine that the peak-to-valley HRV condition is not satisfied if the peak-to-valley HRV value is not less than 50. As such, a peak-to-valley HRV value of 60, for example, would not satisfy the peak-to-valley HRV condition.

Additionally or alternatively, the plurality of conditions may include a cycle length condition. The cycle length is the length of the heart rate cycle (e.g., the length of the period of time of patient 102's heart activity being processed by processing circuitry 302 for detecting a sleep apnea episode). The cycle length condition may be a condition that the cycle length for the heart rate cycle is greater than a lower cycle length threshold and less than an upper cycle length threshold. For example, if the lower cycle length threshold is equal to 25 seconds and the upper cycle length threshold is equal to 100 seconds, then processing circuitry 302 may determine that the cycle length condition is satisfied if the cycle length is greater than 25 seconds and less than 100 seconds. As such, a cycle length of 50 seconds, for example, would satisfy the cycle length condition. Alternatively, processing circuitry 302 determine that the cycle length condition is not satisfied if the cycle length is not greater than 25 seconds and less than 100 seconds. As such, a cycle length of 125 seconds, for example, would not satisfy the cycle length condition.

In some examples, the plurality of conditions may include the peak-to-valley time interval condition, the activity count condition, the peak-to-valley heart rate variation condition, and the cycle length condition. In such examples, determining that the patient has experienced the sleep apnea episode may be based at least in part on each of the conditions of the plurality of conditions being satisfied for the heart rate cycle.

In some examples, medical device system 100 may further determine whether a patient 102 has experienced a sleep apnea episode based on whether one or more conditions of the plurality of conditions are satisfied (508). For example, if each of the one or more conditions is satisfied (e.g., peak-to-valley time interval condition is satisfied) ("YES" branch of 508), processing circuitry 302 may determine that patient 102 has experienced a sleep apnea episode or that the probability that patient 102 has experienced a sleep apnea episode is not low (510). Processing circuitry 302 may then cause the generation of an indication that patient 102 has experienced a sleep apnea event (512). For example, processing circuitry 302 may cause the medical device and/or an external device to generate an indication that patient 102 has experienced a sleep apnea episode.

Alternatively, if one or more of the conditions have not been satisfied ("NO" branch of 508), processing circuitry 302 may determine that patient 102 has not experienced a sleep apnea episode or that the probability that patient 102 has experienced a sleep apnea episode is low (514). Processing circuitry 302 may then cause the generation of an indication that patient 102 has not experienced a sleep apnea event (516). For example, processing circuitry 302 may cause the medical device and/or an external device to generate an indication that patient 102 has not experienced a sleep apnea episode. Alternatively, in some examples, processing circuitry 302 does not generate an indication that patient 102 has experienced a sleep apnea event if patient 102 has not experienced a sleep apnea event.

Processing circuitry 302 may generate an indication that patient 102 has experienced a sleep apnea episode. For example, processing circuitry 302 may cause the medical device or an external device to output an indication that patient 102 has experienced a sleep apnea episode. The external device may include one or more cellular phones, a 'smartphone,' a satellite phone, a notebook computer, a tablet computer, a wearable device, a computer workstation, a personal digital assistant, a handheld computing device, a virtual reality headset, or any other device that may output an indication that patient 102 has experienced a sleep apnea episode. External device may output the indication automatically (e.g., at a pre-determined time of day) and/or in response to input from patient 102 as part of a report or history of patient and in the form of an audible notification, a visual notification, a tactile notification (e.g., a vibration or vibrational pattern), a text prompt, a button prompt, and/or any other notification that may indicate to patient 102 that patient 102 has experienced a sleep apnea episode.

Although not illustrated in FIG. 5, processing circuitry 302 may determine a confidence value, such as a probability, that patient 102 has experienced a sleep apnea episode based on the number of conditions of the plurality of conditions that are satisfied. For example, if only one condition is satisfied, processing circuitry 302 may determine that the confidence value that patient 102 has experienced a sleep apnea episode is low. In another example, if two conditions are satisfied, processing circuitry 302 may determine that the confidence value that patient 102 has experienced a sleep apnea episode is moderate. In another example, if three or more conditions are satisfied, processing circuitry 302 may determine that the confidence value that patient 102 has experienced a sleep apnea episode is high.

Although not illustrated in FIG. 5, medical device system 100 may determine, by processing circuitry 302, that patient 102 has experienced a sleep apnea episode based on one or more conditions being satisfied by at least a non-zero minimum number of additional heart rate cycles other than the current heart rate cycle that occur within a predetermined temporal distance (e.g., amount of time) of the current heart rate cycle. For example, if the minimum number of additional heart rate cycles is equal to 2 and the predetermined temporal distance is equal to 240 seconds, then processing circuitry 302 may determine that patient 102 has experienced a sleep apnea episode based on one or more conditions (e.g., the peak-to-valley time interval condition, the activity count condition, the peak-to-valley heart rate variation condition, the cycle length condition, etc.) being satisfied by 2 additional heart rate cycles other than the current heart rate cycle that occur within 240 seconds of the current heart rate cycle. As such, processing circuitry 302 may determine that patient 102 has experienced a sleep apnea episode based on the activity count condition being satisfied by a heart rate cycle with a temporal distance of 220 seconds of the current heart rate cycle and the peak-to-valley heart rate variation condition being satisfied by a heart rate cycle with a temporal distance of 75 seconds of the current heart rate cycle. Alternatively, processing circuitry 302 may determine that patient 102 has not experienced a sleep apnea episode based on the activity count condition being satisfied by a heart rate cycle with a temporal distance of 300 seconds of the current heart rate cycle and the peak-to-valley heart rate variation condition being satisfied by a heart rate cycle with a temporal distance of 75 seconds of the current heart rate cycle because the heart rate cycle with a temporal distance of 300 seconds did not occur within the predetermined temporal distance of 240 seconds. Additionally or alternatively, in the same example, processing circuitry 302 may determine that patient 102 has not experienced a sleep apnea episode because one or more conditions were not satisfied by 2 or more additional heart rate cycles (e.g., one condition was only satisfied by 1 additional heart rate cycle because only the activity count condition was satisfied by only 1 heart rate cycle with a temporal distance of 75 seconds of the current heart rate cycle).

The reference point for determining the temporal distance may vary. For example, the reference point for determining the temporal distance may be the start of a heart rate cycle, the end of the heart rate cycle, and any point in between the start and end of the heart rate cycle. In some examples, the direction of the temporal distance may vary. That is, the direction of the temporal distance may be retrospective so that heart activity that already occurred may be evaluated, prospective so that heart activity that will occur may be evaluated, or a combination of both.

For example, if the reference point for determining the temporal distance is the start of the heart rate cycle and the predetermined temporal distance is 240 seconds, then processing circuitry 302 may determine that patient 102 has experienced a sleep apnea episode based on heart activity that occurred within any heart rate cycle before the start of the current heart rate cycle with a temporal distance of 240 seconds or less. In another example, processing circuitry 302 may determine that patient 102 has experienced a sleep apnea episode based on heart activity that occurred within any heart rate cycle after the start of the current heart rate cycle with a temporal distance of 240 seconds or less. In yet another example, processing circuitry 302 may determine that patient 102 has experienced a sleep apnea episode based on heart activity occurring within any heart rate cycle before the start of the current heart rate cycle and after the start of the current heart cycle, as long as the heart activity satisfying the one or more conditions occur within a temporal distance of 240 seconds or less.

In another example, if the reference point for determining the temporal distance is the end of the heart rate cycle and the predetermined temporal distance is 240 seconds, then processing circuitry 302 may determine that patient 102 has experienced a sleep apnea episode based on heart activity that occurred within any heart rate cycle before the end of the current heart rate cycle with a temporal distance of 240 seconds or less. Alternatively, processing circuitry 302 may determine that patient 102 has experienced a sleep apnea episode based on heart activity that occurred within any heart rate cycle after the end of the current heart rate cycle with a temporal distance of 240 seconds or less. Alternatively, processing circuitry 302 may determine that patient 102 has experienced a sleep apnea episode based on heart activity that occurred within any heart rate cycle before the end of the current heart rate cycle with a temporal distance of 120 seconds or less and within any heart rate cycle after the end of the current heart rate cycle with a temporal distance of 120 seconds or less.

In another example, if the reference point for determining the temporal distance is the midpoint of the heart rate cycle and the predetermined temporal distance is 240 seconds, then processing circuitry 302 may determine that patient 102 has experienced a sleep apnea episode based on heart activity that occurred within any heart rate cycle before the midpoint of the current heart rate cycle with a temporal distance of 240 seconds or less. Alternatively, processing circuitry 302 may determine that patient 102 has experienced a sleep apnea episode based on heart activity that occurred within any heart rate cycle after the midpoint of the current heart rate cycle with a temporal distance of 240 seconds or less. Alternatively, processing circuitry 302 may determine that patient 102 has experienced a sleep apnea episode based on heart activity that occurred within any heart rate cycle before the midpoint of the current heart rate cycle with a temporal distance of 120 seconds or less and within any heart rate cycle after the midpoint of the current heart rate cycle with a temporal distance of 120 seconds or less.

As used herein, an implantable medical device (IMD) may include, be, or be part of a variety of devices or integrated systems, such as, but not limited to, implantable cardiac monitors (ICMs), implantable pacemakers, including those that deliver cardiac resynchronization therapy (CRT), implantable cardioverter defibrillators (ICDs), diagnostics device, cardiac device, etc. Various examples have been described that include detecting episodes of sleep apnea using cardiac cycle length metrics. In addition, pulmonary therapy may be provided to mitigate the severity of the sleep apnea episode or counter the effects of the sleep apnea episode. Any combination of detection and therapy for sleep apnea episodes is contemplated.

Various aspects of the techniques may be implemented within one or more processing circuitries, including one or more microprocessors, DSPs, ASICs, FPGAs, or any other equivalent integrated or discrete logic circuitry, as well as any combinations of such components, embodied in external devices, such as physician or patient external devices, electrical stimulators, or other devices. The term "processing circuitry" may generally refer to any of the foregoing logic circuitry, alone or in combination with other logic circuitry or any other equivalent circuitry.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. Computer-readable media may include computer-readable storage media forming a tangible, non-transitory medium. Instructions may be executed by one or more processing circuitries, such as one or more DSPs, ASICs, FPGAs, general purpose microprocessors, or other equivalent integrated or discrete logic circuitry. Accordingly, the term "processing circuitry," as used herein may refer to one or more of any of the foregoing structure or any other structure suitable for implementation of the techniques described herein.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external device, a combination of an IMD and external device, an integrated circuit (IC) or a set of ICs, and/or discrete electrical circuitry, residing in an IMD and/or external device.

What is claimed is:

1. A system comprising:
an implantable medical device comprising:
a set of electrodes; and
sensing circuitry configured to sense, via the set of electrodes, a cardiac signal indicating activity of a heart of a patient; and
processing circuitry configured to:
determine a heart rate cycle based on a short-term average of a heart rate and a long-term average of the heart rate, wherein the heart rate cycle defines a period of time of the activity of the heart for detecting an occurrence of a sleep apnea episode, and wherein the short-term average and the long-term average are based on the cardiac signal; and
determine whether a peak-to-valley time interval of the heart rate cycle satisfies a peak-to-valley time interval condition, wherein the peak-to-valley time interval is a time interval between a maximum short-term average of the heart rate during the heart rate cycle and a minimum short-term average of the heart rate during the heart rate cycle; and
wherein the implantable medical device or another medical device is configured to deliver an electrical or airway pressure therapy based at least in part on the processing circuitry determining that the peak-to-valley time interval satisfies the peak-to-valley time interval condition.

2. The system of claim 1, wherein the processing circuitry is configured to determine that the peak-to-valley time interval satisfies the peak-to-valley time interval condition in response to the peak-to-valley time interval being greater than a lower peak-to-valley time threshold and less than an upper peak-to-valley time threshold.

3. The system of claim 1, wherein the processing circuitry is further configured to:

determine whether an activity count of the heart rate cycle satisfies an activity count condition, wherein the activity count indicates a number of time intervals during the heart rate cycle in which an amount of movement of the patient is greater than a minimum movement threshold; and based at least in part on determining that the activity count satisfies the activity count condition and determining that the peak-to-valley time interval satisfies the peak-to-valley time interval condition, output an indication that the sleep apnea episode occurred during the heart rate cycle.

4. The system of claim 3, wherein the processing circuitry is configured to determine that the activity count satisfies the activity count condition in response to the activity count being less than an activity count threshold.

5. The system of claim 4, wherein the activity count threshold is equal to 8.

6. The system of claim 1, wherein the processing circuitry is further configured to:

determine whether a peak-to-valley heart rate variation value of the heart rate cycle satisfies a peak-to-valley heart rate variation condition, wherein the peak-to-valley heart rate variation value indicates a difference between the maximum short-term average of the heart rate during the heart rate cycle and the minimum short-term average of the heart rate during the heart rate cycle; and based at least in part on determining that the peak-to-valley heart rate variation value satisfies the peak-to-valley heart rate variation condition and determining that the peak-to-valley time interval satisfies the peak-to-valley time interval condition, output an indication that the sleep apnea episode occurred during the heart rate cycle.

7. The system of claim 6, wherein the processing circuitry is configured to determine that the peak-to-valley heart rate variation value satisfies the peak-to-valley heart rate variation condition in response to the peak-to-valley heart rate variation value being between a lower peak-to-valley heart rate variation threshold and an upper peak-to-valley heart rate variation threshold.

8. The system of claim 7, wherein at least one of the lower peak-to-valley heart rate variation threshold is equal to 6 beats per minute, or the upper peak-to-valley heart rate variation threshold is equal to 50 beats per minute.

9. The system of claim 1, wherein the processing circuitry is further configured to:

determine whether a cycle length of the heart rate cycle satisfies a cycle length condition, wherein the cycle length indicates a length of the heart rate cycle; and based at least in part on determining that the cycle length satisfies the cycle length condition and determining that the peak-to-valley time interval satisfies the peak-tovalley time interval condition, output an indication that the sleep apnea episode occurred during the heart rate cycle.

10. The system of claim 9, wherein the processing circuitry is configured to determine that the cycle length satisfies the cycle length condition in response to the cycle length being greater than a lower cycle length threshold and less than an upper cycle length threshold.

11. The system of claim 1, wherein the heart rate cycle is a current heart rate cycle, and wherein the processing circuitry is further configured to:

determine whether at least one additional heart rate cycle that occurs within a predetermined temporal distance of the current heart rate cycle satisfies at least one condition of a plurality of conditions, wherein each condition of the plurality of conditions is associated with the occurrence of the sleep apnea episode; and based at least in part on determining that the at least one additional heart rate cycle satisfies the at least one condition of the plurality of conditions, output an indication that the sleep apnea episode occurred during the current heart rate cycle.

12. The system of claim 11, wherein the plurality of conditions comprises at least one of the peak-to-valley time interval condition, an activity count condition, a peak-to-valley heart rate variation condition, or a cycle length condition.

13. The system of claim 11, wherein the predetermined temporal distance is 240 seconds.

14. The system of claim 1, wherein the implantable medical device comprises the processing circuitry, and wherein the system further comprises an external device configured to receive an indication that the sleep apnea episode occurred during the heart rate cycle.

15. The system of claim 1, wherein, to determine the heart rate cycle, the processing circuitry is configured to:

determine a start of the heart rate cycle based on a first time the short-term average of the heart rate changes from being less than the long-term average of the heart rate to being greater than the long-term average of the heart rate; and determine an end of the heart rate cycle based on a second time the short-term average of the heart rate changes from being less than the long-term average of the heart rate to being greater than the long-term average of the heart rate of the patient.

16. An implantable medical device comprising:

a set of electrodes;

sensing circuitry configured to sense, via the set of electrodes, a cardiac signal indicating activity of a heart of a patient; and processing circuitry configured to:

determine a heart rate cycle based on a short-term average of a heart rate and a long-term average of the heart rate, wherein the heart rate cycle defines a period of time of the activity of the heart for detecting an occurrence of a sleep apnea episode, and wherein the short-term average and the long-term average are based on the cardiac signal;

determine whether a peak-to-valley time interval of the heart rate cycle satisfies a peak-to-valley time interval condition, wherein the peak-to-valley time interval is a time interval between a maximum short-term average of the heart rate during the heart rate cycle and a minimum short-term average of the heart rate during the heart rate cycle; and based at least in part on determining that the peak-to-valley time interval satisfies the peak-to-valley time interval condition, output an indication that the sleep apnea episode occurred during the heart rate cycle.

17. The implantable medical device of claim 16, wherein the processing circuitry is configured to determine that the peak-to-valley time interval satisfies the peak-to-valley time interval condition in response to the peak-to-valley time interval being greater than a lower peak-to-valley time threshold and less than an upper peak-to-valley time threshold.

18. The implantable medical device of claim 17, wherein the processing circuitry is further configured to:

determine whether an activity count of the heart rate cycle satisfies an activity count condition, wherein the activity count indicates a number of time intervals during the heart rate cycle in which an amount of movement of the patient is greater than a minimum movement threshold; and based at least in part on determining that the activity count satisfies the activity count condition and determining that the peak-to-valley time interval satisfies the peakto-valley time interval condition, output the indication that the sleep apnea episode occurred during the heart rate cycle.

19. A method comprising:

determining, by processing circuitry, a heart rate cycle based on a short-term average of a heart rate and a long-term average of the heart rate, wherein the heart rate cycle defines a period of time of activity of a heart of a patient for detecting an occurrence of a sleep apnea episode, and wherein the short-term average and the long-term average are based on a cardiac signal that indicates the activity of the heart of the patient;

determining, by the processing circuitry, whether a peak-to-valley time interval of the heart rate cycle satisfies a peak-to-valley time interval condition, wherein the peak-to-valley time interval is a time interval between a maximum short-term average of the heart rate during the heart rate cycle and a minimum short-term average of the heart rate during the heart rate cycle; and delivering, by a medical device, an electrical or airway pressure therapy based at least in part on the processing circuitry determining that the peak-to-valley time interval satisfies the peak-to-valley time interval condition.

* * * * *